US009675307B2

(12) United States Patent
Ofuji et al.

(10) Patent No.: US 9,675,307 B2
(45) Date of Patent: Jun. 13, 2017

(54) RADIATION IMAGING APPARATUS, RADIATION IMAGING SYSTEM, AND CONTROL METHOD OF RADIATION IMAGING SYSTEM

(71) Applicant: CANON KABUSHIKI KAISHA, Tokyo (JP)

(72) Inventors: Masato Ofuji, Takasaki (JP); Minoru Watanabe, Honjo (JP); Keigo Yokoyama, Honjo (JP); Jun Kawanabe, Kumagaya (JP); Kentaro Fujiyoshi, Tokyo (JP); Hiroshi Wayama, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 29 days.

(21) Appl. No.: 14/729,248

(22) Filed: Jun. 3, 2015

(65) Prior Publication Data

US 2015/0362601 A1  Dec. 17, 2015

(30) Foreign Application Priority Data

Jun. 13, 2014 (JP) ................................ 2014-122743
May 26, 2015 (JP) ................................ 2015-106732

(51) Int. Cl.
*G01T 1/20*  (2006.01)
*G01T 1/208*  (2006.01)
(Continued)

(52) U.S. Cl.
CPC ............ *A61B 6/4233* (2013.01); *A61B 6/542* (2013.01); *G01N 23/04* (2013.01); *G01T 1/17* (2013.01);
(Continued)

(58) Field of Classification Search
None
See application file for complete search history.

(56) References Cited

U.S. PATENT DOCUMENTS 6,403,964 B1 *  6/2002  Kyyhkynen ............ G01T 1/243
                                                   250/366
7,386,089 B2 *  6/2008  Endo ..................... A61B 6/482
                                                   378/114
(Continued)

FOREIGN PATENT DOCUMENTS

JP  2012-247354  12/2012
JP  2013-135390  7/2013

OTHER PUBLICATIONS

U.S. Appl. No. 14/802,297, filed Jul. 17, 2015.
U.S. Appl. No. 14/817,301, filed Aug. 4, 2015.

*Primary Examiner* — Michael Logie
(74) *Attorney, Agent, or Firm* — Fitzpatrick, Cella, Harper & Scinto (57) ABSTRACT

A radiation imaging apparatus includes a plurality of pixels for acquiring a radiation image and a plurality of sensors for detecting radiation, a processing unit for sampling outputs from sensors constituting an effective sensor group, out of the plurality of sensors, and outputting information for control of irradiation in accordance with the sampled outputs. In a first period after the irradiation to the radiation imaging apparatus starts, the processing unit excludes, from the effective sensor group, a sensor, a value corresponding to an output from which has exceeded a first threshold, out of the plurality of sensors, and in a second period after the first period, the processing unit outputs the information in accordance with outputs from the sensors constituting the effective sensor group.

12 Claims, 10 Drawing Sheets

(51) Int. Cl.
*A61B 6/00* (2006.01)
*G01N 23/04* (2006.01)
*G01T 1/24* (2006.01)
*G01T 1/17* (2006.01)

(52) U.S. Cl.
CPC ........ G01T 1/247 (2013.01); *G01N 2223/501* (2013.01)

(56) References Cited

U.S. PATENT DOCUMENTS

| | | | |
|---|---|---|---|
| 7,514,663 B2 | 4/2009 | Yagi et al. | 250/208.1 |
| 7,541,591 B2 | 6/2009 | Endo et al. | 250/369 |
| 7,573,038 B2 | 8/2009 | Yokoyama et al. | 250/370.09 |
| 7,718,973 B2 | 5/2010 | Endo et al. | 250/370.08 |
| 2005/0147203 A1* | 7/2005 | Ross | A61B 6/032 378/19 |
| 2011/0317054 A1 | 12/2011 | Kameshima et al. | 348/302 |
| 2012/0075507 A1* | 3/2012 | Yamazaki | H04N 5/32 348/241 |
| 2012/0305791 A1* | 12/2012 | Watanabe | G01T 1/247 250/394 |
| 2013/0202086 A1* | 8/2013 | Tsuji | G01T 1/026 378/62 |
| 2015/0055752 A1* | 2/2015 | Takahashi | H04N 5/32 378/62 |
| 2015/0164458 A1* | 6/2015 | Tajima | A61B 6/4283 378/97 |

* cited by examiner

RADIATION IMAGING APPARATUS, RADIATION IMAGING SYSTEM, AND CONTROL METHOD OF RADIATION IMAGING SYSTEM

BACKGROUND OF THE INVENTION

Field of the Invention

The present invention relates to a radiation imaging apparatus, a radiation imaging system, and a control method of the radiation imaging system.

Description of the Related Art

There is a radiation imaging apparatus including a pixel array in which pixels each including a conversion element configured to convert radiation into charges, and a switching element such as a thin-film transistor are arrayed. Recently, multi-functionality of radiation imaging apparatuses of this type is examined. As one of these functions, incorporation of an automatic exposure control (AEC) function is receiving attention. Automatic exposure control in the radiation imaging apparatus can be used for, for example, detection of the start of irradiation with radiation from a radiation source, decision of the timing to stop irradiation with radiation, and detection of the dose or accumulated dose of radiation.

Japanese Patent Laid-Open No. 2012-247354 discloses a radiation image detection apparatus that detects the start and end of irradiation with radiation by monitoring an output from a high-sensitivity detection element selected in advance from a plurality of detection elements arranged in an imaging region where a plurality of pixels are arrayed. The detection of the end of irradiation with radiation in the radiation image detection apparatus disclosed in Japanese Patent Laid-Open No. 2012-247354 is detection of the timing when irradiation with radiation ends, and is not detection of the timing to end irradiation with radiation. The radiation image detection apparatus disclosed in Japanese Patent Laid-Open No. 2012-247354 monitors an output from a preselected high-sensitivity detection element, that is, a specific detection element, and cannot detect the exposure state of a portion (for example, a soft tissue or bone) regarding diagnosis. For example, when radiation entering a detection element whose output is monitored enters the detection element without passing through an object, the exposure state of a portion regarding diagnosis in the object cannot be detected depending on monitoring of an output from the detection element.

SUMMARY OF THE INVENTION

The present invention provides a technique advantageous for exposure control of a portion regarding diagnosis in an object.

One of aspects of the present invention provides a radiation imaging apparatus including a plurality of pixels configured to acquire a radiation image, and a plurality of sensors configured to detect radiation, the apparatus comprising: a processing unit configured to sample outputs from sensors constituting an effective sensor group, out of the plurality of sensors, and output information for control of irradiation with radiation in accordance with the sampled outputs, wherein in a first period after the irradiation with radiation to the radiation imaging apparatus starts, the processing unit excludes, from the effective sensor group, a sensor, a value corresponding to an output from which has exceeded a first threshold, out of the plurality of sensors, and in a second period after the first period, the processing unit outputs the information in accordance with outputs from the sensors constituting the effective sensor group, and wherein a frequency of sampling of each sensor constituting the effective sensor group is higher in the second period than in the first period.

Further features of the present invention will become apparent from the following description of exemplary embodiments with reference to the attached drawings.

DESCRIPTION OF THE EMBODIMENTS

Exemplary embodiments of the present invention will now be described with reference to the accompanying drawings.

Figure 1A:
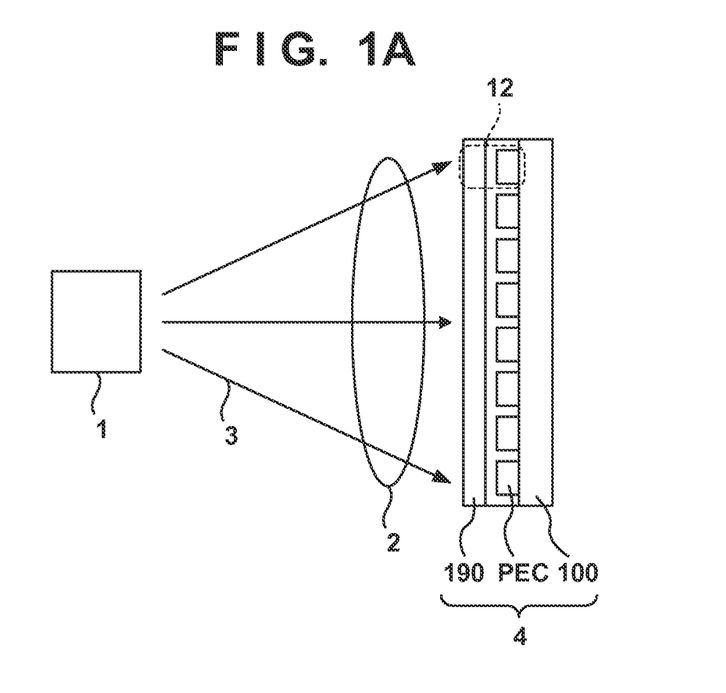
FIGS. 1A and 1B are views showing radiation imaging systems according to two embodiments of the present invention.
Figure 1B:
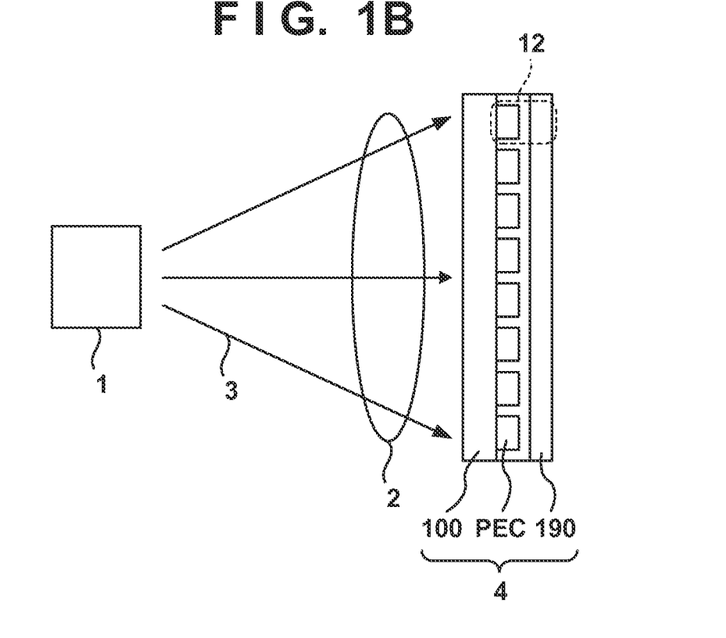

FIG. 1A schematically shows the constitution of a radiation imaging system according to one embodiment of the present invention. FIG. 1B schematically shows the constitution of a radiation imaging system according to another embodiment of the present invention. Each of these radiation imaging systems includes a radiation source 1 that emits radiation 3 such as an X-ray, and a radiation imaging apparatus 4. The radiation 3 emitted from the radiation source 1 is transmitted through an object 2 and enters the radiation imaging apparatus 4.

The radiation imaging apparatus 4 can include a plurality of photoelectric conversion elements (PECs) two-dimensionally arrayed to constitute an array having a plurality of rows and a plurality of columns, a substrate 100 that supports or holds the plurality of PECs, and a scintillator 190. The scintillator 190 converts radiation into light such as visible light. The PEC is constituted by, for example, a photodiode, and converts, into an electrical signal, light converted by the scintillator 190. The PEC and the scintillator 190 constitute a conversion element 12 that converts radiation into an electrical signal. The scintillator 190 can be shared by a plurality of conversion elements 12.

In the embodiment shown in FIG. 1A, the scintillator 190 faces the radiation source 1. In the embodiment shown in FIG. 1B, the substrate 100 faces the radiation source 1, and the radiation 3 passes through the substrate 100 and the array constituted by the plurality of PECs, and enters the scintillator 190. Then, light converted by the scintillator 190 enters the PECs.

Figure 2:
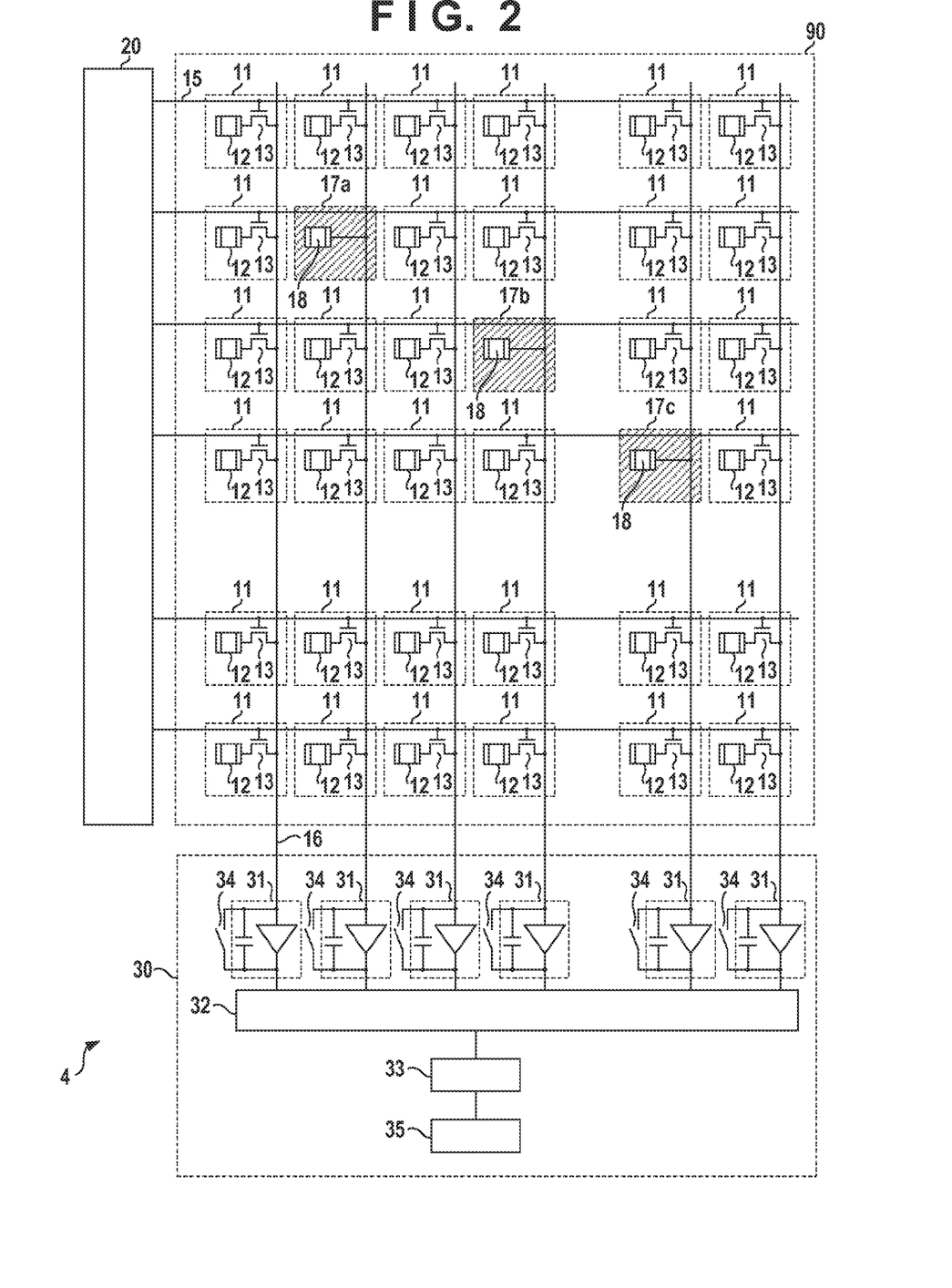
FIG. 2 is a view showing the constitution of a radiation imaging apparatus according to the first embodiment of the present invention.

FIG. 2 shows the constitution of a radiation imaging apparatus 4 according to the first embodiment of the present invention. The radiation imaging apparatus 4 includes a plurality of pixels 11 for acquiring a radiation image, and a plurality of sensors 17, that is, 17a, 17b, and 17c for detecting radiation. The numerical signs 17a, 17b, and 17c are used to discriminate the plurality of sensors 17 from each other.

The plurality of pixels 11 are two-dimensionally arrayed to constitute an array having a plurality of rows and a plurality of columns, and this array constitutes an imaging region 90. Each pixel 11 includes a conversion element 12 that converts radiation into an electrical signal, and a switch 13. The conversion element 12 may be constituted by a PEC and a scintillator, as described above, or by an element that directly converts radiation into an electrical signal. The conversion element 12 can include the first electrode (also called a discrete electrode or readout electrode), and the second electrode (also called a common electrode). The first electrode is connected to a corresponding column signal line 16 via the switch 13. The second electrode can be connected to a bias line (not shown) for applying a bias potential to the conversion element 12.

The plurality of sensors 17 include conversion elements 18 that convert radiation into an electrical signal. The conversion element 18 of each sensor 17 may be constituted by a PEC and a scintillator, or by an element that directly converts radiation into an electrical signal. In the former constitution, the scintillator for the conversion element 18 can be shared by a scintillator for the pixel 11. In the first embodiment, the sensor 17 is directly connected to the corresponding column signal line 16. The sensor 17 is used to acquire information for controlling irradiation with radiation to the radiation imaging apparatus 4. More specifically, the sensor 17 can be used to acquire information representing the accumulated value of irradiated radiation. Based on this information, a command to stop irradiation with radiation can be output to the radiation source 1. The sensor 17 may also be used to detect the start of irradiation with radiation to the radiation imaging apparatus 4.

The radiation imaging apparatus 4 further includes a row selecting unit 20 and a processing unit 30. The row selecting unit 20 selects a row of the array constituting the imaging region 90 by driving, to an active level, a row selecting line 15 of the row to be selected, out of a plurality of row selecting lines 15. When the row selecting line 15 is driven to the active level, the switches 13 of the pixels 11 on this row are turned on, and the first electrodes of the conversion elements 12 of the pixels 11 on this row are connected to the column signal lines 16.

The processing unit 30 reads out signals output to the column signal lines 16 from the pixels 11 on the row selected by the row selecting unit 20. The processing unit 30 can also read out signals output from the sensors 17 to the column signal lines 16. In a state in which the row selecting lines 15 of all rows are driven to an inactive level, only signals from the sensors 17 are output to the column signal lines 16, and the processing unit 30 can read out the signals.

The processing unit 30 can include amplifiers 31, a multiplexer 32, an A/D converter 33, reset switches 34, and a calculating unit 35. Each amplifier 31 detects (amplifies) a signal output to the column signal line 16. The amplifier 31 can be, for example, an integrating amplifier. Here, the plurality of amplifiers 31 are arranged so that one amplifier 31 corresponds to one column signal line 16. Each reset switch 34 resets the amplifier 31 by short-circuiting the input terminal and output terminal of the amplifier 31, and also resets the potential of the column signal line 16.

The multiplexer 32 sequentially selects the plurality of amplifiers 31, and outputs from the selected amplifiers 31 to the A/D converter 33. The A/D converter 33 converts a signal (analog signal) output from the multiplexer 32 into a digital signal. The calculating unit 35 processes the signal output from the A/D converter 33 and outputs the processed result. The calculating unit 35 may output the signal output from the A/D converter 33 without any processing.

In addition, the calculating unit 35 processes a signal provided from the sensor 17 via the amplifier 31, the multiplexer 32, and the A/D converter 33, and outputs the processed result. Alternatively, the calculating unit 35 may output a signal provided from the sensor 17 via the amplifier 31, the multiplexer 32, and the A/D converter 33 without any processing. Note that the A/D converter 33 may be omitted, and the calculating unit 35 may be constituted to output an analog signal and/or a signal obtained by processing the analog signal.

As will be described in detail below, the first embodiment adopts a concept "effective sensor group" in order to exclude, from monitoring targets, the sensor 17, an output from which need not be monitored, out of the plurality of sensors 17. The calculating unit 35 (processing unit 30) outputs information for controlling irradiation with radiation in accordance with outputs from the sensors 17 constituting the effective sensor group, out of the plurality of sensors 17. That is, the calculating unit 35 does not monitor an output from the sensor 17 excluded from the effective sensor group.

For example, in the first period after irradiation with radiation to the radiation imaging apparatus 4 starts, the calculating unit 35 excludes, from the effective sensor group, the sensor 17, the accumulated value (value corresponding to an output) of an output from which has exceeded a first threshold Th1, out of the plurality of sensors 17. For example, the sensors 17, the accumulated values of outputs from which have exceeded the first threshold Th1, can be sequentially excluded from the effective sensor group. In another example, all the sensors 17, the accumulated values of outputs from which have exceeded the first threshold Th1 till the end of the first period can be excluded at once from the effective sensor group after the end of the first period.

The sensor 17, the accumulated value of an output from which has exceeded the first threshold Th1 in the first period, is handled as the sensor 17 not arranged in a region of interest for exposure control (control of the stop of radiation), and is thus excluded from the effective sensor group.

In the second period after the first period, the calculating unit 35 (processing unit 30) outputs information (for example, a command to instruct the radiation source 1 to stop irradiation with radiation) for controlling irradiation with radiation in accordance with outputs from the sensors 17 constituting the effective sensor group. In the second period, only the sensors 17 constituting the effective sensor group become monitoring targets. The frequency at which the calculating unit 35 samples an output from the sensor 17 serving as the monitoring target via the amplifier 31, the multiplexer 32, and the A/D converter 33 can be increased to improve the monitoring accuracy (that is, the decision accuracy of the timing to stop irradiation with radiation). That is, the frequency at which the calculating unit 35 samples an output from each sensor 17 constituting the effective sensor group is higher in the second period than in the first period.

Figure 3A:
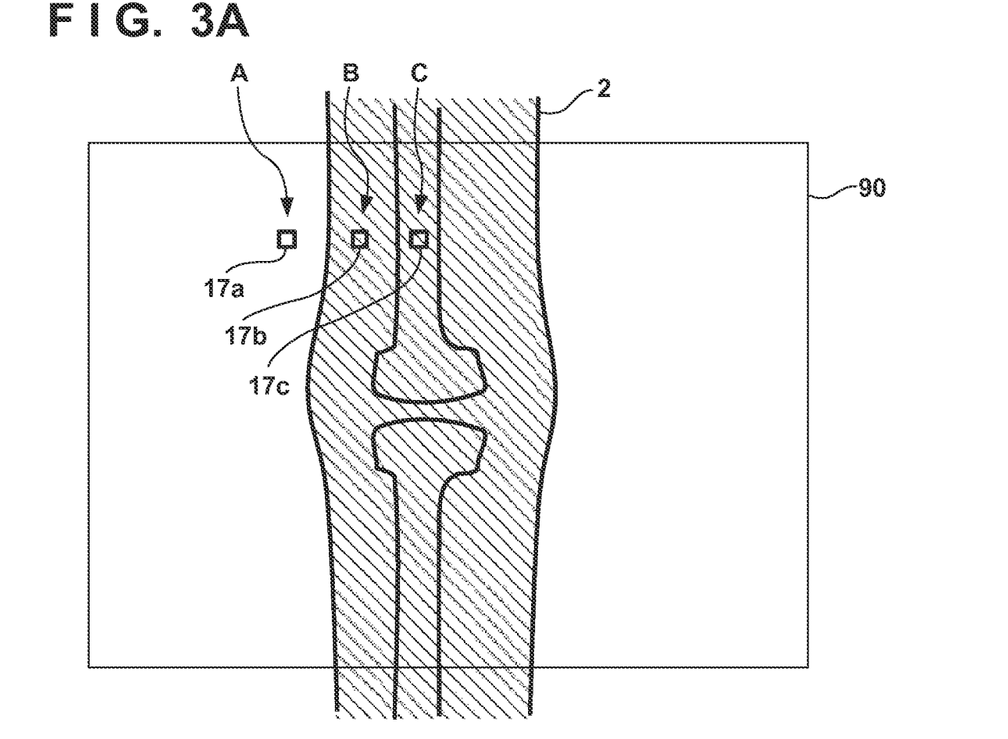
FIGS. 3A and 3B are views showing an example of the use of sensors according to the first embodiment of the present invention.

FIG. 3A shows an example of the arrangement of the plurality of sensors 17a, 17b, and 17c in the imaging region 90 and an example of an object 2. In this example, the object 2 is the knee joint of a human body. The sensor 17a is arranged in a region A where the object 2 does not exist and which radiation from the radiation source 1 enters while hardly attenuating. The sensor 17b is arranged in a region B which radiation transmitted through a muscle tissue enters. The sensor 17c is arranged in a region C where a bone tissue serving as a region of interest exists. Irradiation with radiation should be decided based on an accumulated dose to the region C serving as a region of interest. The operator of the radiation imaging system sets in advance the knee joint as the inspection target (or the bony septum as the region of interest) in the radiation imaging system.

Figure 3B:
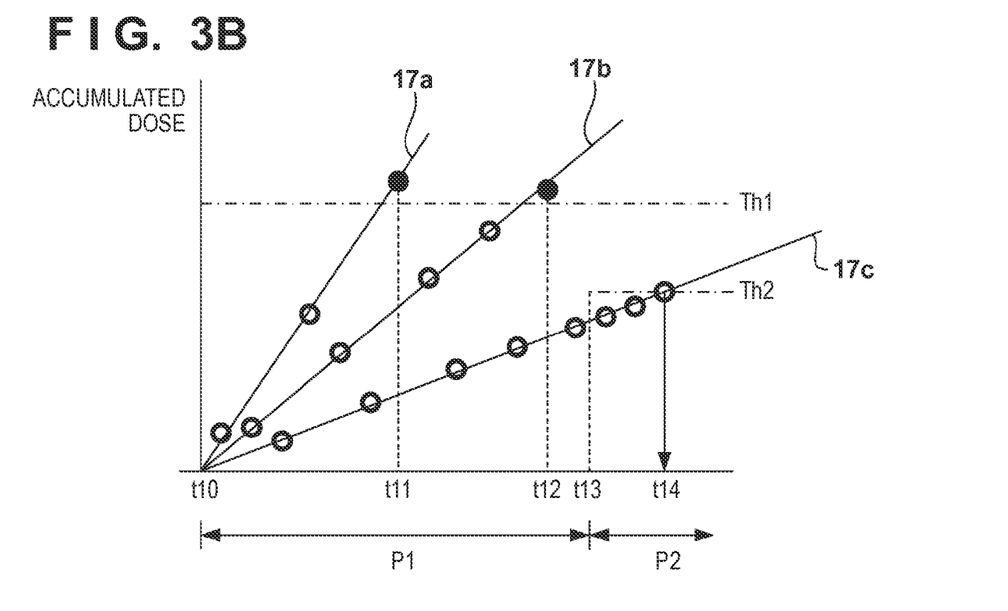

FIG. 3B schematically shows a temporal change of the accumulated dose of radiation calculated by the calculating unit 35 based on signals from the sensors 17a, 17b, and 17c. The start time of irradiation with radiation is t10. The start of irradiation with radiation can be detected based on, for example, a signal (a command to instruct the radiation source 1 to start irradiation with radiation) from a controller that controls the radiation source 1. Alternatively, the start of irradiation with radiation can be detected by monitoring an output from the sensor 17 or another sensor by the processing unit 30.

After start time t10, the calculating unit 35 calculates the accumulated values of outputs from the sensors 17a, 17b, and 17c in the order of the sensors 17a, 17b, and 17c. The interval (sampling period) until an output from the next sensor 17 is sampled after sampling an output from a given sensor 17 is determined in accordance with the specifications of the processing unit 30. A period from t10 to t13 is a first period P1 described above, and a period after t13 is a second period P2 described above.

In the first period P1, the calculating unit 35 excludes, from the effective sensor group, a sensor, the accumulated value (accumulated dose) of an output from which has exceeded the first threshold Th1, out of the plurality of sensors 17a, 17b, and 17c. In the example of FIG. 3B, it is determined that the accumulated value of an output from the sensor 17a has exceeded the threshold Th1 at time t11, and the accumulated value of an output from the sensor 17b has exceeded the threshold Th1 at time t12. The first threshold Th1 is a threshold for discriminating a sensor arranged outside the region of interest. The calculating unit 35 can decide the first threshold Th1 by looking up a lookup table (not shown) or the like based on the setting representing that the inspection target is the knee joint (or the region of interest is the bony septum). Alternatively, the operator may set the first threshold Th1.

In this example, the sensor 17a is excluded from the effective sensor group at time t11, and the sensor 17b is excluded from the effective sensor group at time t12. As a result, the number of monitoring target sensors is decreased by one at time t11, reducing the burden on the calculating unit 35 for monitoring outputs from all sensors constituting the effective sensor group. Also, the number of monitoring target sensors is further decreased by one at time t12, further reducing the burden on the calculating unit 35 for monitoring outputs from all sensors constituting the effective sensor group.

Note that the processing of excluding, from the effective sensor group, the sensors 17a and 17b, the accumulated values of outputs from which have exceeded the first threshold Th1, may be performed at once after the lapse of the first period P1.

In the second period P2 after the first period P1, the calculating unit 35 outputs information (for example, a command to instruct the radiation source 1 to stop irradiation with radiation) for controlling irradiation with radiation in accordance with a signal from the sensor 17c constituting the effective sensor group. More specifically, when the accumulated value of an output from one (sensor 17c) of the sensors constituting the effective sensor group exceeds a second threshold Th2, the processing unit 30 (calculating unit 35) outputs information for controlling irradiation with radiation. In this case, the second threshold Th2 is smaller than the first threshold Th1.

In the second period P2, the unnecessary sensors 17a and 17b arranged outside the region of interest, out of the plurality of sensors 17a, 17b, and 17c, do not exist in the effective sensor group. Hence, the frequency at which an output from the sensor 17c constituting the effective sensor group is sampled is increased to improve the monitoring accuracy (that is, the decision accuracy of the timing to stop irradiation with radiation).

In the first period P1, the comparison between the accumulated value of a sensor output and the second threshold Th2 is not performed. This is because the accumulated values of outputs from the sensors 17a and 17b should exceed the second threshold Th2 in the first period P1, but it is insignificant to detect this.

The shift from the first period P1 to the second period P2 can be performed when, for example, one of the following conditions is satisfied:

(1) A predetermined time has elapsed after (detection of) the start of irradiation with radiation.

(2) The number of sensors, the accumulated values of outputs from which have exceeded the first threshold Th1 (or the ratio of this number to the total number of sensors), has reached a predetermined number (or a predetermined ratio). Alternatively, a predetermined time has elapsed after this instant.

(3) The number of sensors, the accumulated values of outputs from which have exceeded the first threshold Th1, is saturated.

Figure 4:
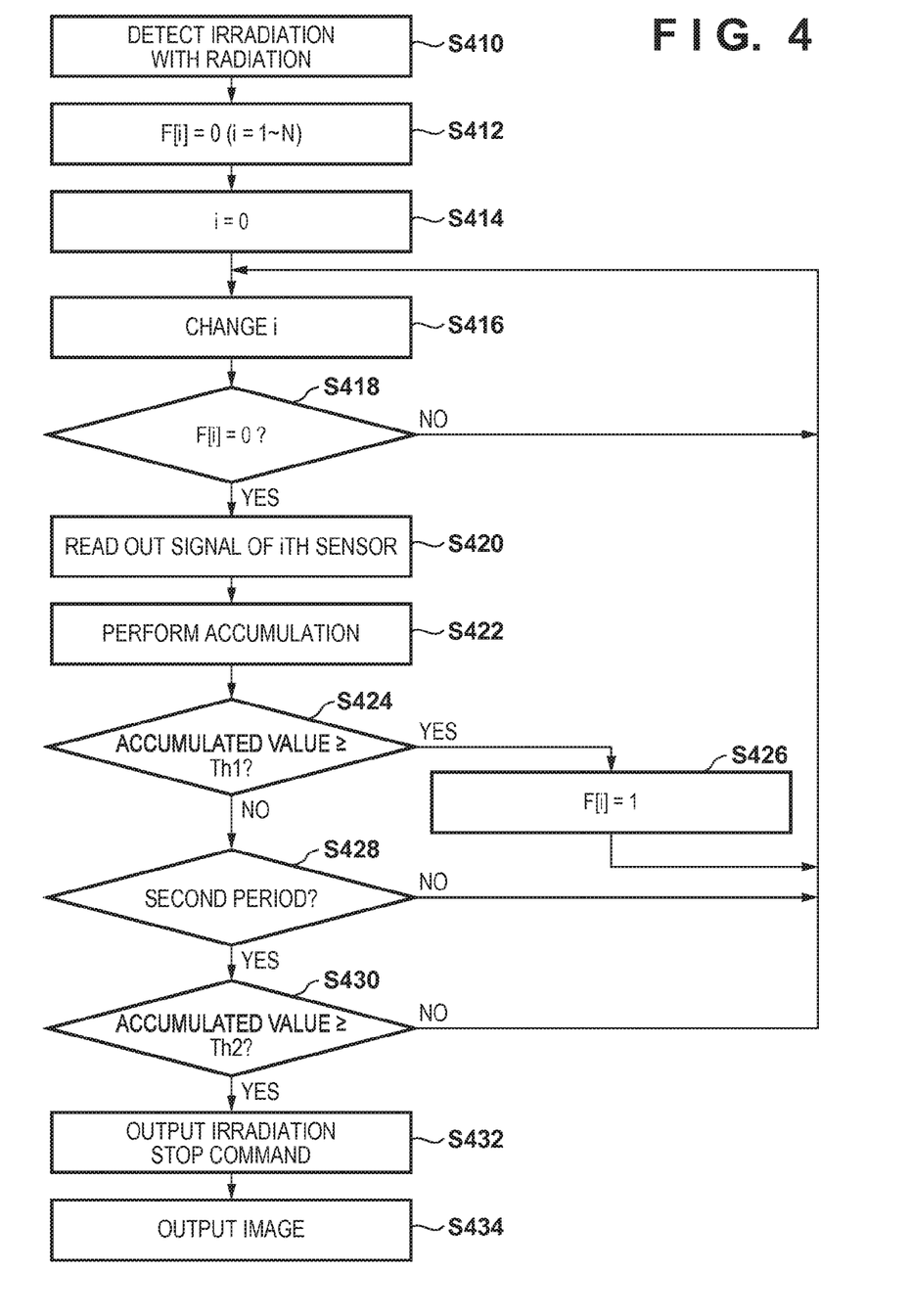
FIG. 4 is a flowchart showing the operation of the radiation imaging apparatus according to the first embodiment of the present invention.

FIG. 4 shows the sequence of processing to be executed by the calculating unit 35 (processing unit 30). In step S410, the calculating unit 35 detects irradiation with radiation. In step S412, the calculating unit 35 sets, to be 0, a flag F[i] (i=1 to N) for managing the effective sensor group, in which i is the number for discriminating the plurality of sensors 17 from each other. F[i]=0 represents that the ith sensor 17 belongs to the effective sensor group. F[i]=1 represents that the ith sensor 17 does not belong to the effective sensor group (that is, the ith sensor 17 is excluded from the effective sensor group). In step S414, the calculating unit 35 sets i to be 0.

In step S416, the calculating unit 35 changes the i value in order to change the sensor 17 of interest. In step S418, the calculating unit 35 determines whether the ith sensor 17 belongs to the effective sensor group. If the ith sensor 17 belongs to the effective sensor group, the calculating unit 35 advances to step S420. If the ith sensor 17 does not belong to the effective sensor group, the calculating unit 35 returns to step S416.

In step S420, the calculating unit 35 reads out the signal of the ith sensor 17. In step S422, the calculating unit 35 calculates the accumulated value of an output from the ith sensor 17. In step S424, the calculating unit 35 determines whether the accumulated value (that is, a value corresponding to an output) of an output from the ith sensor 17 has exceeded the first threshold Th1. If the calculating unit 35 determines that the accumulated value of an output from the ith sensor 17 has exceeded the first threshold Th1, it sets F[i] to be 1 in step S426 in order to exclude the ith sensor 17 from the effective sensor group, and returns to step S416.

In step S428, the calculating unit 35 determines whether the condition to shift from the first period P1 to the second period P2 has been satisfied. If the shift condition is not satisfied, the calculating unit 35 returns to step S416. If the shift condition is satisfied, the calculating unit 35 advances to step S430.

In step S430, the calculating unit 35 determines whether the accumulated value of an output from the ith sensor 17 has exceeded the second threshold Th2. If the calculating unit 35 determines that the accumulated value of an output from the ith sensor 17 has not exceeded the second threshold Th2, it returns to step S416. If the calculating unit 35 determines that the accumulated value of an output from the ith sensor 17 has exceeded the second threshold Th2, it advances to step S432.

In step S432, the calculating unit 35 outputs information (for example, a command to instruct the radiation source 1 to stop irradiation with radiation) for controlling irradiation with radiation. That is, in step S432, the calculating unit 35 outputs information (for example, a command to instruct the radiation source 1 to stop irradiation with radiation) for controlling irradiation with radiation in accordance with the accumulated value of an output from the ith sensor 17. At this time, the calculating unit 35 may simply output information representing that the accumulated value of an output from the ith sensor 17 has exceeded the second threshold Th2. Upon receiving this output, an external apparatus can output the command to instruct the radiation source 1 to stop irradiation with radiation.

In step S434, the calculating unit 35 outputs an image captured by the plurality of pixels 11 of the imaging region 90. More specifically, the calculating unit 35 reads out signals from the respective pixels 11 constituting a plurality of rows and a plurality of columns, and outputs them.

For example, the sampling period can be 30 μsec, and the radiation irradiation time in the case of still image capturing can be about 10 msec. In the imaging region 90, for example, several tens of sensors 17 can be arranged. If the number of sensors 17 constituting the effective sensor group is decreased to about one to three in the first period P1, the time taken to sample, by the calculating unit 35, outputs from all the sensors 17 to be monitored becomes about 30 μsec to 90 μsec. This time is sufficiently short with respect to the radiation irradiation time, so the stop of irradiation with radiation can be controlled with satisfactory accuracy.

In the first period P1 and/or the second period P2, the calculating unit 35 may output an output from the sensor 17 or a signal or data obtained by processing the output.

In the above-described embodiment, the operator of the radiation imaging system sets an inspection target in the radiation imaging system. However, the calculating unit 35 may execute preliminary imaging and automatically determine an inspection target by pattern matching, image processing, or the like based on the result of the preliminary imaging. Further, the calculating unit 35 may set the first threshold Th1 and the second threshold Th2 in accordance with the result of the automatic determination.

The sampling period of an output from the sensor 17 by the calculating unit 35 need not be constant. For example, when the number of monitoring target sensors 17 is large, the sampling period can be shortened to give priority to the readout speed. After the number of monitoring target sensors 17 becomes smaller than a predetermined number, the sampling period may be prolonged to place importance on noise reduction.

Figure 5:
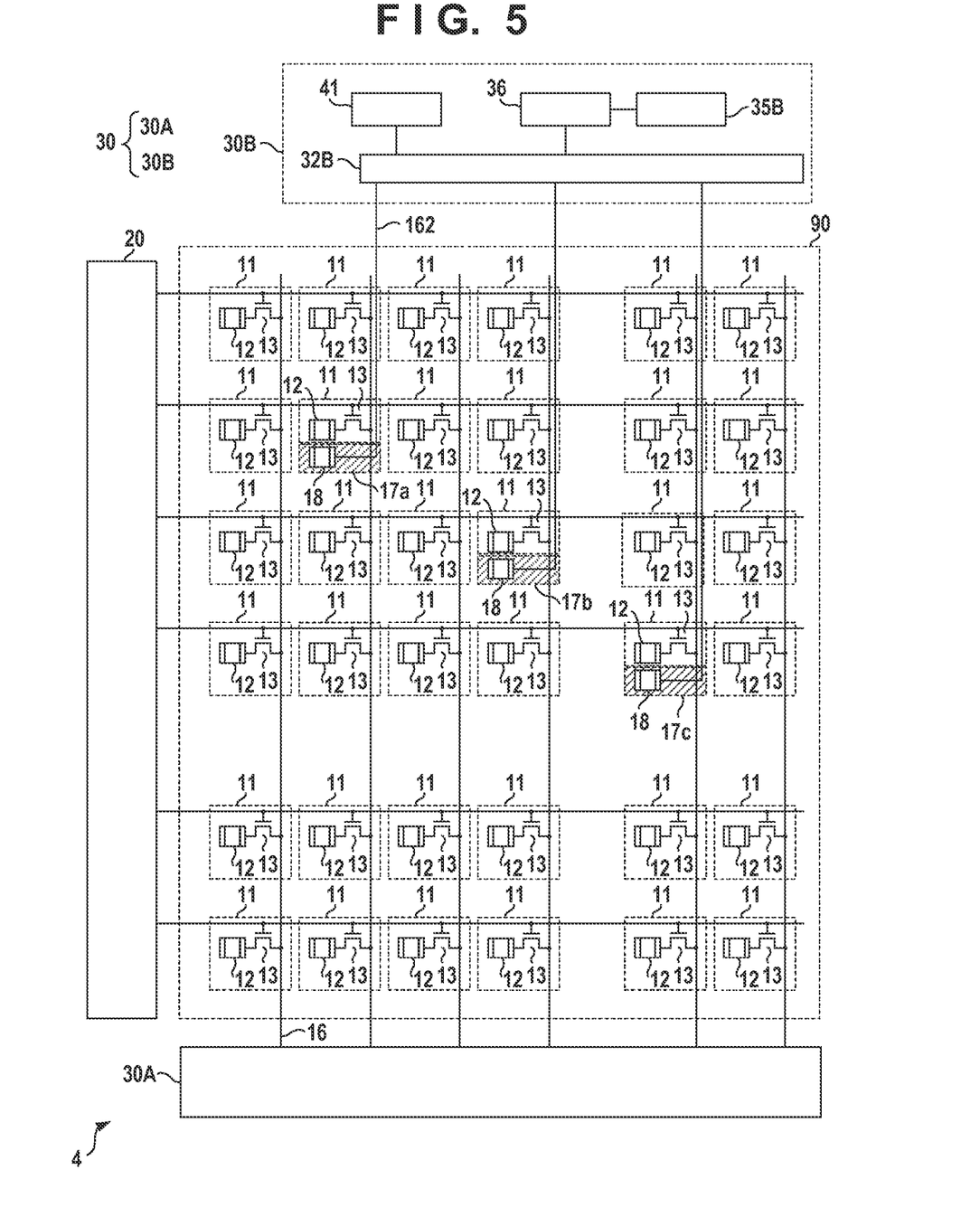
FIG. 5 is a view showing the constitution of a radiation imaging apparatus according to the second embodiment of the present invention.

A radiation imaging apparatus 4 according to the second embodiment of the present invention will be described below with reference to FIG. 5. Note that details not mentioned in the second embodiment can comply with the first embodiment. In the first embodiment, the pixel 11 is not arranged at a position (position specified by a row and a column) at which the sensor 17 is arranged. In the second embodiment, a pixel 11 is arranged at even a position at which a sensor 17 is arranged. In other words, the numbers of pixels 11 arranged on respective rows constituting the array of an imaging region 90 are equal to each other.

In the second embodiment, signals from the sensors 17 are read out via detection signal lines 162 arranged separately from column signal lines 16. The processing unit 30 in the first embodiment is divided into a processing unit 30A and a processing unit 30B in the second embodiment. The processing unit 30A is constituted to read out signals output to the column signal lines 16 from the pixels 11 on a row selected by a row selecting unit 20. The processing unit 30A can have the same constitution as that of the processing unit 30 according to the first embodiment. The processing unit 30B includes a multiplexer 32B, a selecting unit 41, a readout unit 36, and a calculating unit 35B. The multiplexer 32B selects one of the plurality of detection signal lines 162 in accordance with a selection signal from the selecting unit 41. That is, the multiplexer 32B selects one of the plurality of sensors 17 in accordance with a selection signal from the selecting unit 41. The readout unit 36 reads out a signal from the sensor 17 selected by the multiplexer 32B. As for processing of the signal output from the sensor 17, the calculating unit 35B performs the same processing as that of the calculating unit 35 according to the first embodiment. In the second embodiment, the operation of the processing unit 30A can be stopped in the first period P1 and the second period P2, and the power consumption can therefore be reduced.

Figure 6:
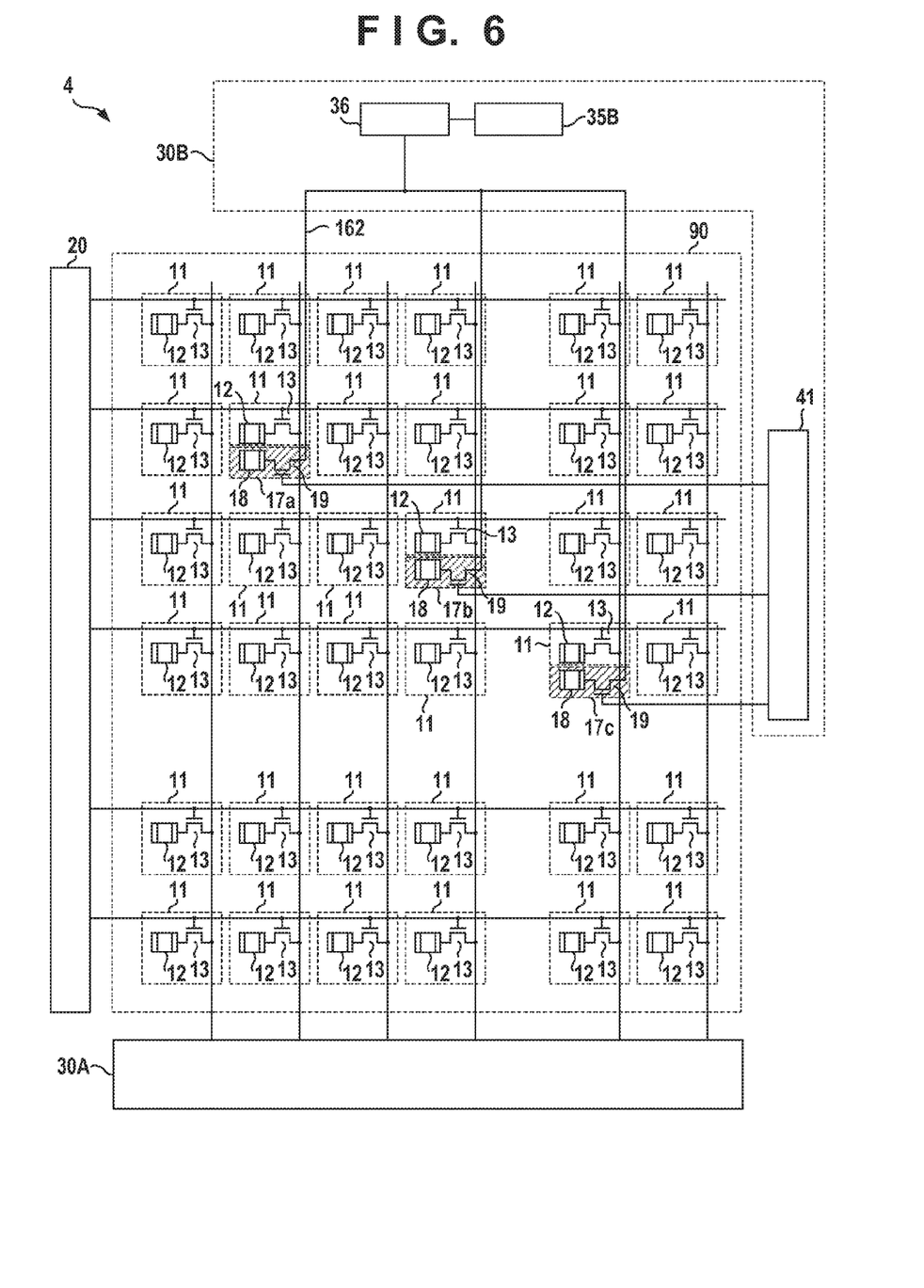
FIG. 6 is a view showing the constitution of a radiation imaging apparatus according to the third embodiment of the present invention.

A radiation imaging apparatus 4 according to the third embodiment of the present invention will be described below with reference to FIG. 6. The third embodiment is a modification of the second embodiment, and details not mentioned in the third embodiment can comply with the second embodiment.

In the third embodiment, each of sensors 17, that is, sensors 17a, 17b, and 17c includes a switch 19 between a conversion element 18 and a detection signal line 162. A selecting unit 41 controls the switch 19 to select one sensor 17 from the plurality of sensors 17, and provide a signal from the selected sensor 17 to a readout unit 36.

Figure 10:
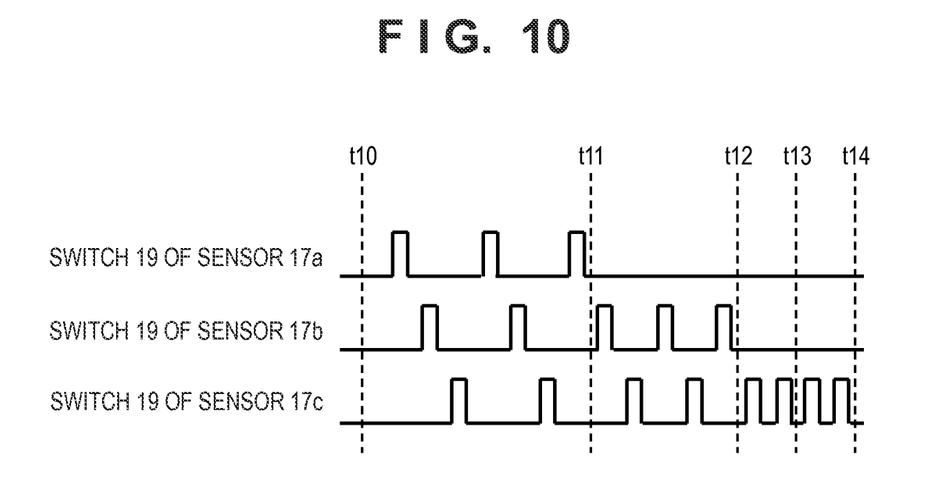
FIG. 10 is a timing chart showing a voltage signal output from a selecting unit 41 according to the third embodiment of the present invention.

FIG. 10 is a timing chart showing a voltage signal output from the selecting unit 41 to the switch 19 corresponding to each sensor 17. Each switch 19 is ON in the High (active level) period, and OFF in the Low (inactive level) period. In this manner, each switch 19 selects the monitoring target sensor 17, and a calculating unit 35B samples an output from each sensor 17 by the same method as that in the first embodiment. As a result, the accumulated dose of radiation as in FIG. 3B can be obtained.

Since the switch 19 of the sensor 17 not serving as a monitoring target is not selected, the power consumption in the selecting unit 41 can be reduced. Since the unnecessary switch 19 need not be opened/closed, noise generated in the radiation imaging apparatus 4 along with control of the switch 19 can be minimized, and the accuracy of a signal obtained by the calculating unit 35B can also be increased.

The fourth embodiment of the present invention will be described below with reference to FIGS. 7A and 7B. In the fourth embodiment, the operation of the calculating unit 35 or 35B in the first to third embodiments is changed. Details not mentioned here can comply with the first to third embodiments. In the fourth embodiment, a region where the accumulated dose is lower than a criterion, such as a region where radiation is cut off by a metal implant or the like, is defined as the outside of a region of interest. In other words, in the fourth embodiment, even a sensor arranged in a region where the accumulated dose is lower than the criterion is also excluded from an effective sensor group.

Figure 7A:
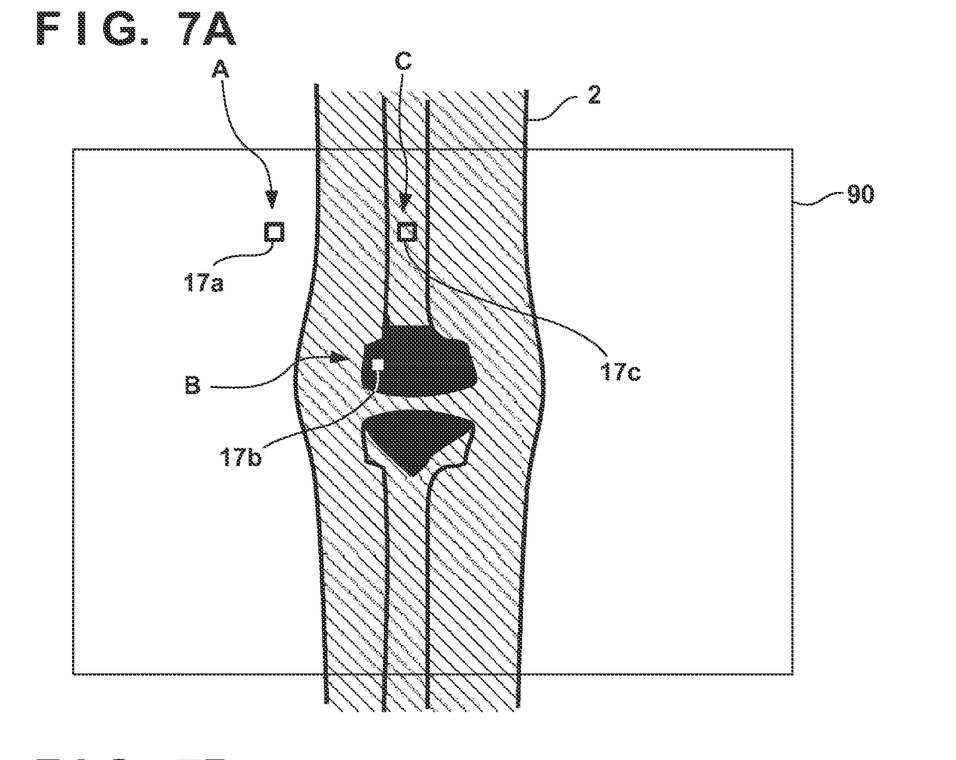
FIGS. 7A and 7B are views showing an example of the use of sensors according to the fourth embodiment of the present invention.

FIG. 7A shows an example of the arrangement of a plurality of sensors 17a, 17b, and 17c in an imaging region 90 and an example of an object 2. In this example, the object 2 is the knee joint of a human body, and a metal implant is buried in the knee joint. In this example, the sensor 17a is arranged in a region A where the object 2 does not exist and which radiation from a radiation source 1 enters while hardly attenuating. The sensor 17b is arranged in a region B where radiation is cut off by the metal implant. The sensor 17c is arranged in a region C where a bone tissue serving as a region of interest exists. Irradiation with radiation should be decided based on an accumulated dose to the region C serving as a region of interest.

Figure 7B:
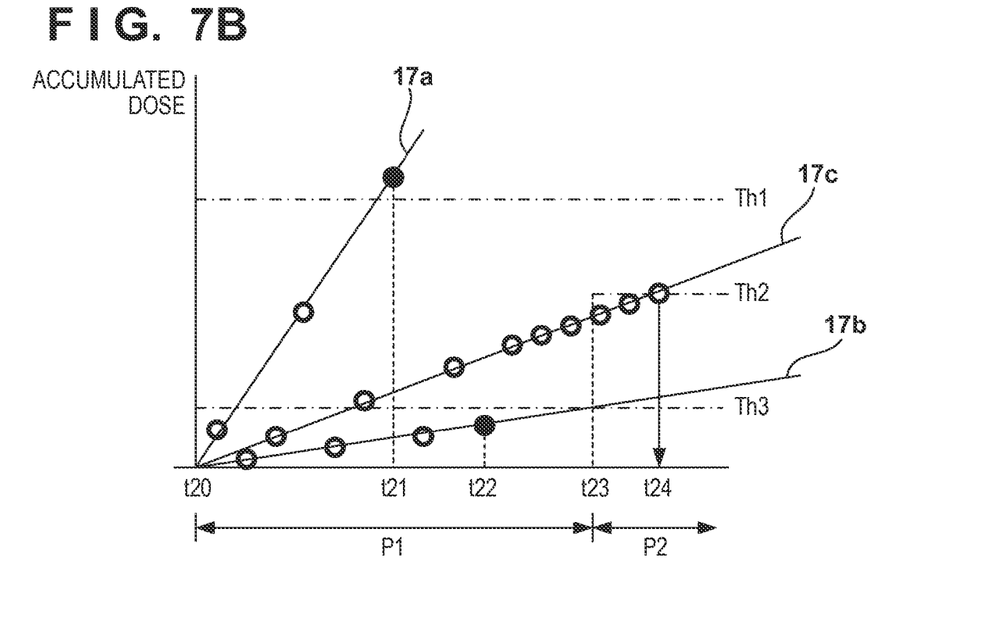

FIG. 7B schematically shows a temporal change of the accumulated dose of radiation obtained by the calculating unit 35 based on signals from the sensors 17a, 17b, and 17c. The start time of irradiation with radiation is t20. As described above, the start time of irradiation with radiation is t10. The start of irradiation with radiation can be detected based on, for example, a signal (a command to instruct the radiation source 1 to start irradiation with radiation) from a controller that controls the radiation source 1. Alternatively, the start of irradiation with radiation can be detected by monitoring an output from the sensor 17 or another sensor by a processing unit 30.

In the fourth embodiment, a third threshold Th3 is used in addition to a first threshold Th1 and a second threshold Th2. Similar to the first threshold Th1, the third threshold Th3 is a threshold for discriminating a sensor arranged outside the region of interest. A calculating unit 35 can decide the third threshold Th3 by looking up a lookup table (not shown) or the like based on the setting representing that the inspection target is the knee joint (or the region of interest is the bony septum). Alternatively, the operator may set the first threshold Th1.

The calculating unit 35 excludes, from the effective sensor group, the sensor 17b, the accumulated value of an output from which is smaller than the third threshold Th3 after given time t22 in the first period P1. That is, the calculating unit 35 determines that the sensor 17b, the accumulated value of an output from which is smaller than the third threshold Th3 after given time t22 in the first period P1, is a region outside the region of interest. In the fourth embodiment, even a region where the accumulated dose is lower than the criterion is excluded from the effective sensor group as for sensors of the region of interest, so the number of monitoring target sensors can be decreased. Thus, the frequency at which the calculating unit 35 samples an output from the sensor 17 serving as a monitoring target via an amplifier 31, a multiplexer 32, and an A/D converter 33 can be increased to improve the monitoring accuracy. Times t23 and t24 are the same as times t13 and t14, respectively.

According to the fourth embodiment, the monitoring accuracy is improved. Thus, the fourth embodiment is effective even when a region (for example, the lung field in chest imaging) that easily transmits radiation is imaged as a region of interest, when the sensor 17 is abnormal owing to a manufacturing defect, or the like.

The fifth embodiment of the present invention will be described below with reference to FIGS. 8A and 8B. In the fifth embodiment, the operation of the calculating unit 35 or 35B in the first to third embodiments is changed. The fifth embodiment is also applicable to the fourth embodiment. In the fifth embodiment, at least one sensor out of at least two sensors 17, the accumulated values of outputs from which are approximate to each other, out of a plurality of sensors 17, is excluded from an effective sensor group.

Figure 8A:
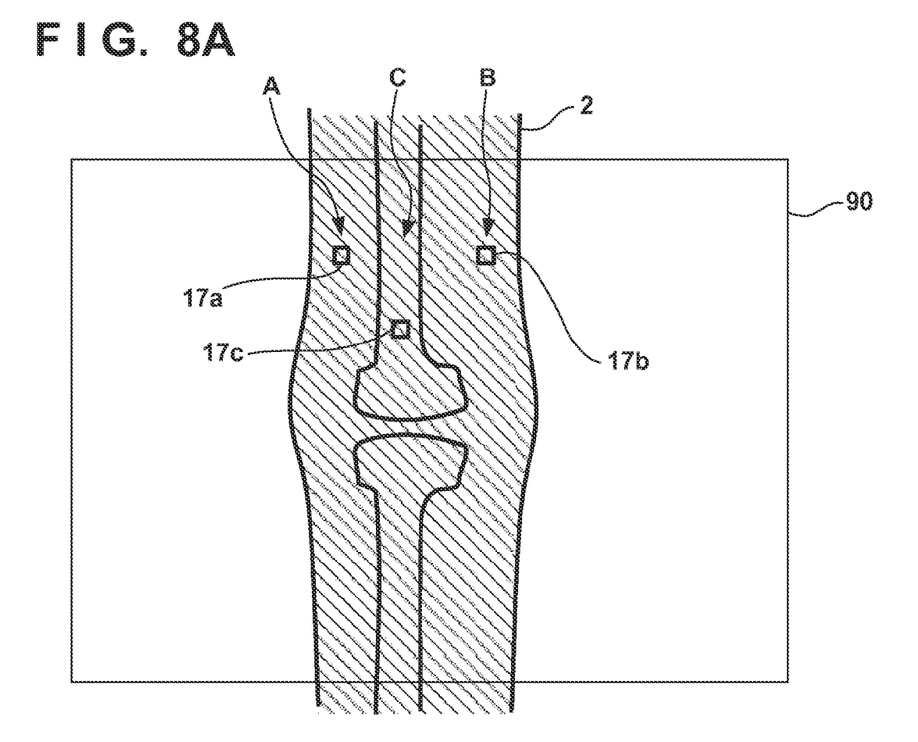
FIGS. 8A and 8B are views showing an example of the use of sensors according to the fifth embodiment of the present invention.

FIG. 8A shows an example of the arrangement of a plurality of sensors 17a, 17b, and 17c in an imaging region 90 and an example of an object 2. In this example, the object 2 is the knee joint of a human body. In this example, the sensors 17a and 17b are arranged in regions A and B where radiation transmitted through a muscle tissue enters, respectively. The sensor 17c is arranged in a region C where a bone tissue serving as a region of interest exists. Irradiation with radiation should be decided based on an accumulated dose to the region C serving as a region of interest.

Figure 8B:
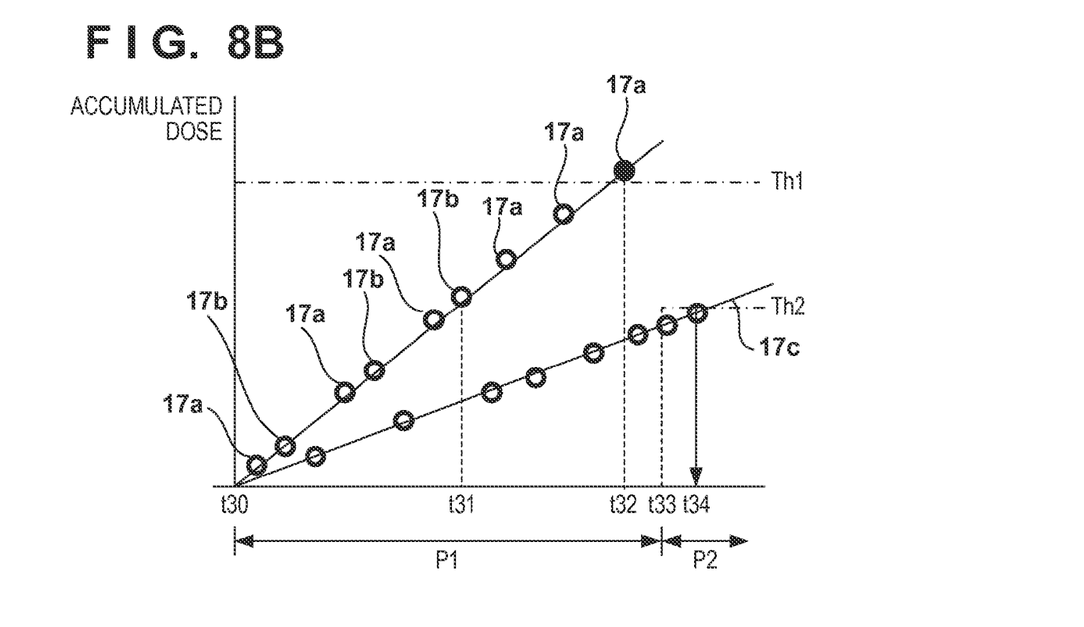

FIG. 8B schematically shows a temporal change of the accumulated dose of radiation obtained by a calculating unit 35 based on signals from the sensors 17a, 17b, and 17c. The start time of irradiation with radiation is t30. The accumulated values of outputs from the sensors 17a and 17b are approximate to each other. For example, at time t31 in the first period, the calculating unit 35 can determine that the accumulated values of outputs from the sensors 17a and 17b are approximate to each other. Thus, at time t31, the calculating unit 35 excludes one of the sensors 17a and 17b from the effective sensor group. For example, assume that the sensor 17b is excluded from the effective sensor group.

At time t32, the calculating unit 35 determines that the accumulated value of an output from the sensor 17a has exceeded a threshold Th1. The subsequent processing is the same as that in the first embodiment. The sampling frequency can be increased by excluding, from the effective sensor group, at least one sensor out of at least two sensors 17, the accumulated values of outputs from which are approximate to each other, out of the plurality of sensors 17.

A modification of each of the above-described embodiments will be explained. In each of the above-described embodiments, sensors constituting the effective sensor group are decided based on the accumulated values (corresponding to accumulated doses) of outputs from the sensors. However, this is merely one practicing form of the present invention. Sensors constituting the effective sensor group may be decided based on, for example, the output values (corresponding to irradiation intensities of radiation) of the sensors.

In each of the above-described embodiments, the signals (charges) of pixels and sensors are read out by a destructive readout method. However, the present invention is also applicable to a radiation imaging apparatus including APS (Active Pixel Sensor) pixels and sensors. In this case, a signal from the sensor can be directly used as a signal representing an accumulated dose. The physical amount of a signal to be read out from the sensor can be an arbitrary physical amount such as charges, current, or voltage.

Figure 9:
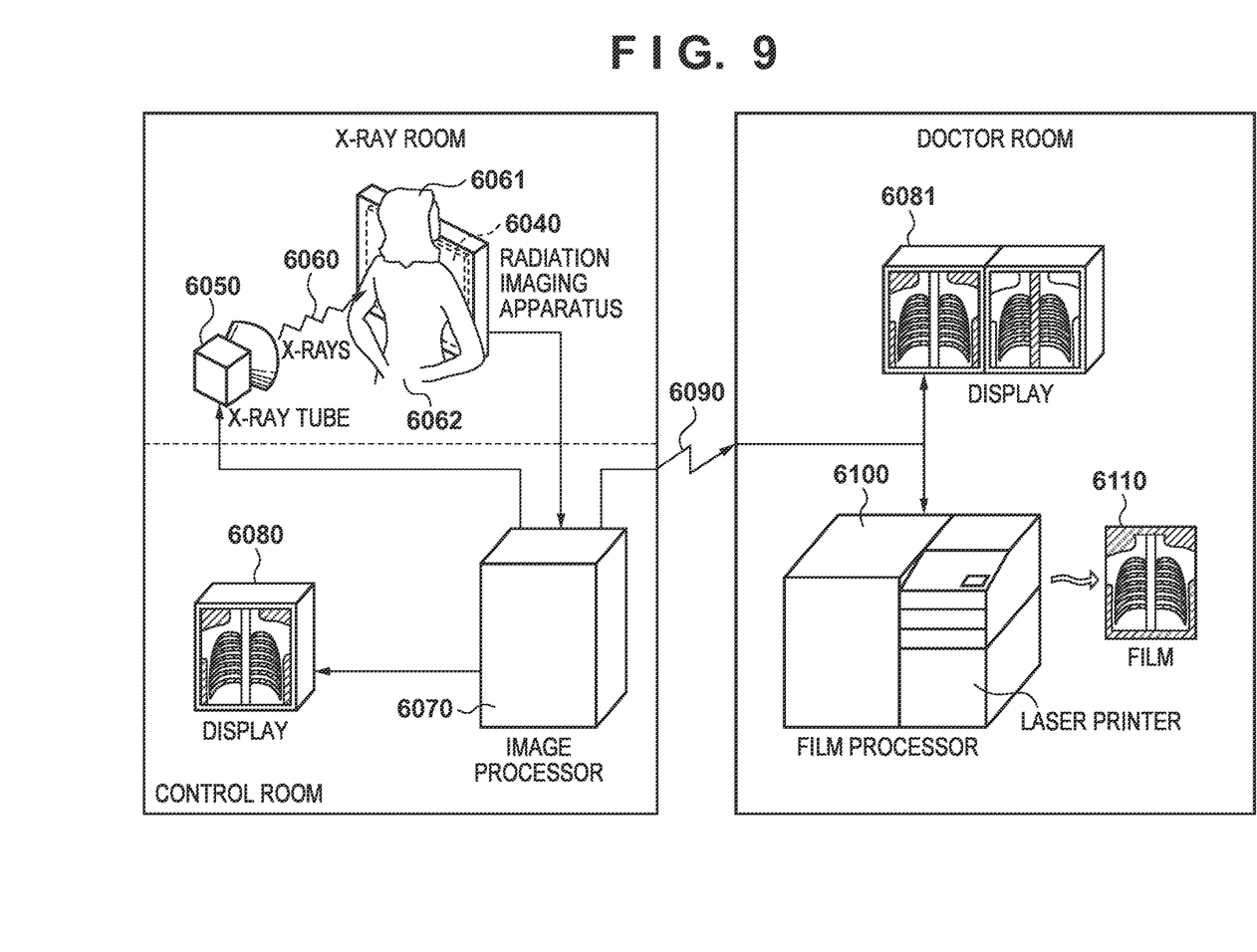
FIG. 9 is a view showing an example of the more detailed constitution of a radiation imaging system.

FIG. 9 shows an example of the more detailed constitution of the radiation imaging system. X-rays 6060 generated by an X-ray tube 6050 serving as a radiation source pass through a chest 6062 of a patient or object 6061 and enter each conversion element 12 included in a radiation imaging apparatus 6040. The incident X-rays include information about the inside of the body of the object 6061. The conversion element 12 converts the radiation into charges in correspondence with the entrance of the X-rays, obtaining electrical information. This information is converted into digital data, undergoes image processing by an image processor 6070 serving as a signal processing means, and can be observed on a display 6080 serving as a display means in a control room.

Also, this information can be transferred to a remote place by a transmission processing means such as a telephone line 6090, and can be displayed on a display 6081 serving as a display means in a doctor room or the like at another place, or can be saved on a recording unit such as an optical disk. Even a doctor at the remote place can make a diagnosis. A film processor 6100 serving as a recording means can also record the information on a film 6110 serving as a recording medium.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-122743, filed Jun. 13, 2014 and 2015-106732, filed May 26, 2015, which are hereby incorporated by reference herein in their entirety.

What is claimed is:

1. A radiation imaging apparatus including a plurality of pixels configured to acquire a radiation image, and a plurality of sensors configured to detect radiation, the apparatus comprising:

a processing unit configured to sample outputs from sensors constituting an effective sensor group, out of the plurality of sensors, and output information for control of irradiation with radiation in accordance with the sampled outputs, wherein in a first period after the irradiation of radiation to the radiation imaging apparatus starts, the processing unit excludes a first sensor from the effective sensor group, wherein a value corresponding to an output from the first sensor has exceeded a first threshold, and in a second period after the first period, the processing unit outputs the information in accordance with outputs from the sensors constituting the effective sensor group excluding the first sensor, and wherein a frequency of sampling of each sensor constituting the effective sensor group is higher in the second period than in the first period.

2. The apparatus according to claim 1, wherein in the second period, the processing unit outputs the information when a value corresponding to an output from one of the sensors constituting the effective sensor group exceeds a second threshold smaller than the first threshold.

3. The apparatus according to claim 2, wherein in the second period, the processing unit outputs the information when the value corresponding to the output from one of the sensors constituting the effective sensor group exceeds the second threshold smaller than the first threshold.

4. The apparatus according to claim 2, wherein in the first period, the processing unit excludes, from the effective sensor group, a sensor, a value corresponding to an output from which does not exceed a third threshold smaller than the second threshold, out of the plurality of sensors.

5. The apparatus according to claim 2, wherein the first threshold and the second threshold are set in accordance with an inspection target.

6. The apparatus according to claim 1, wherein the processing unit excludes, from the effective sensor group, at least one sensor out of at least two sensors, values corresponding to outputs from which are approximate to each other, out of the sensors constituting the effective sensor group.

7. The apparatus according to claim 1, wherein the information includes a command to instruct a stop of the irradiation with radiation.

8. The apparatus according to claim 1, wherein the plurality of pixels are arrayed to constitute a plurality of rows and a plurality of columns, and
the numbers of pixels arranged on the respective rows are equal to each other.

9. The apparatus according to claim 1, wherein the first threshold is set in accordance with an inspection target.

10. The apparatus according to claim 1, wherein the value corresponding to the output is an accumulated value of the output.

11. A radiation imaging system comprising:
a radiation source configured to generate radiation; and
a radiation imaging apparatus defined in claim 1.

12. A method of controlling a radiation imaging system including a radiation source configured to generate radiation, and a radiation imaging apparatus,
the radiation imaging apparatus including a plurality of pixels configured to acquire a radiation image, and a plurality of sensors configured to detect radiation,
the control method comprising:
a step of sampling outputs from sensors constituting an effective sensor group, out of the plurality of sensors, and stopping irradiation with radiation by the radiation source in accordance with the sampled outputs, the step including:
a first step of, after the irradiation of radiation to the radiation imaging apparatus starts, excluding a first sensor from the effective sensor group, wherein a value corresponding to an output from the first sensor has exceeded a first threshold; and
a second step of, after the first step, stopping the irradiation with radiation by the radiation source when a value corresponding to an output from one of the sensors constituting the effective sensor group excluding the first sensor exceeds a second threshold smaller than the first threshold,
wherein a frequency of sampling of each sensor constituting the effective sensor group is higher in the second step than in the first step.

\* \* \* \* \*